United States Patent [19]

Kleinschroth et al.

[11] Patent Number: 4,751,228

[45] Date of Patent: Jun. 14, 1988

[54] 1,6-NAPHTHYRIDINE DERIVATIVES

[75] Inventors: Jörgen Kleinschroth, Denzlingen; Karl Mannhardt, Elzach-Oberprechtal; Johannes Hartenstein, Stegen-Wittental; Gerhard Satzinger, Denzlingen; Dieter Muster, Elzach-Prechtal; Wolfgang Steinbrecher, Gundelfingen; Bernd Wagner, Denzlingen; Hartmut Osswald, Waldkirch, all of Fed. Rep. of Germany

[73] Assignee: Goedecke Aktiengesellschaft, Berlin, Fed. Rep. of Germany

[21] Appl. No.: 7,691

[22] Filed: Jan. 28, 1987

[30] Foreign Application Priority Data

Feb. 22, 1986 [DE] Fed. Rep. of Germany ....... 3605743

[51] Int. Cl.⁴ .................. A61K 31/435; C07D 471/04
[52] U.S. Cl. .................................... 514/300; 544/362; 546/122; 546/123
[58] Field of Search ................. 546/123, 122; 514/300

[56] References Cited

FOREIGN PATENT DOCUMENTS 133530 2/1985 European Pat. Off. .
173933 3/1986 European Pat. Off. .

Primary Examiner—Mary C. Lee
Assistant Examiner—Bernard I. Dentz
Attorney, Agent, or Firm—Elizabeth M. Anderson

[57] ABSTRACT

The present invention provides 1,6-naphthyridine derivatives of formula

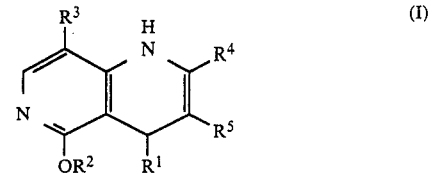

wherein $R^1$ is an unsubstituted or substituted aromatic or heteroaromatic ring or an unsubstituted or substituted condensed aromatic or heterocyclic ring system, $R^2$ is a straight-chained or branched alkyl radical containing up to 4 carbon atoms, a benzyl radical or a straight-chained or branched, substituted or unsubstituted aminoalkyl radical containing up to 8 carbon atoms, $R^3$ is a hydrogen atom, a straight-chained or branched alkyl radical or an alkoxycarbonyl radical, in each case containing up to 4 carbon atoms, $R^4$ is a straight-chained or branched hydrocarbon radical containing up to 21 carbon atoms, which can also contain oxygen, sulphur, nitrogen or halogen atoms and is optionally substituted by carbocyclic or heterocyclic ring systems, or is an amino, cyano, formyl, halogenomethyl or dihalomethyl radical and $R^5$ is an alkoxycarbonyl radical or an unsubstituted or substituted carboxamide radical with, in each case, up to 21 carbon atoms which can also contain oxygen, sulphur or nitrogen atoms and is optionally substituted by carbocyclic or heterocyclic ring systems or is a carboxyl or cyano group as well as the pharmaceutically acceptable salts thereof.

The compounds are useful for blood vessel diseases.

The present invention also provides processes for the preparation of these 1,6-naphthyridine derivatives, pharmaceutical compositions containing them, and methods for using them.

10 Claims, No Drawings

1,6-NAPHTHYRIDINE DERIVATIVES

BACKGROUND OF THE INVENTION

The present invention is concerned with new 1,6-naphthyridine derivatives, with processes for the preparation thereof and with pharmaceutical compositions containing them.

SUMMARY AND DETAILED DESCRIPTION

The new 1,6-naphthyridine derivatives according to the present invention are compounds of the formula

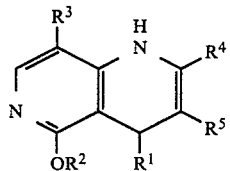

(I)

wherein $R^1$ is an unsubstituted or substituted aromatic or heteroaromatic ring or an unsubstituted or substituted condensed aromatic or heterocyclic ring system, $R^2$ is a straight-chained or branched alkyl radical containing up to 4 carbon atoms, a benzyl radical or a straight-chained or branched, substituted or unsubstituted aminoalkyl radical containing up to 8 carbon atoms, $R^3$ is a hydrogen atom, a straight-chained or branched alkyl radical or an alkoxycarbonyl radical, in each case containing up to 4 carbon atoms, $R^4$ is a straight-chained or branched hydrocarbon radical containing up to 21 carbon atoms, which can also contain oxygen, sulphur, nitrogen or halogen atoms and is optionally substituted by carbocyclic or heterocyclic ring systems, or is an amino, cyano, formyl, halogenomethyl or dihalomethyl radical and $R^5$ is an alkoxycarbonyl radical or an unsubstituted or substituted carboxamide radical with, in each case, up to 21 carbon atoms which can also contain oxygen, sulphur or nitrogen atoms and is optionally substituted by carbocyclic or heterocyclic ring systems or is a carboxyl or cyano group; as well as the pharmaceutically acceptable salts thereof.

Preferred compounds of formula (I) are 1,6-naphthyridine derivatives in which $R^1$ is an unsubstituted phenyl radical or a phenyl radical which is mono- or disubstituted by halogen, cyano, nitro, lower alkyl, lower alkoxy, difluoromethoxy, difluoromethylthio, trifluoromethoxy, lower alkylenedioxy, for example methylenedioxy, lower alkylamino, especially dimethylamino or diethylamino, methylthio or trifluoromethyl radicals, or is a naphthyl, 2-pyridyl, 2-thienyl or 2,1,3-benzoxadiazolyl radical, $R^2$ is a straight-chained or branched alkyl radical containing up to 4 carbon atoms or a 1-dimethylamino-2-propyl radical, $R^3$ is a hydrogen atom, $R^4$ is a methyl radical, an amino, cyano or formyl group, a halomethyl or dihalomethyl radical, a hydroxymethyl, alkoxymethyl, benzyloxymethyl, hydroxyalkoxymethyl, benzyloxyalkylmethyl or alkoxyalkoxymethyl radical, an unsubstituted or substituted aminomethyl, aminoalkoxymethyl or aminoalkylthiomethyl radical or optionally a quarternary salt thereof, an unsubstituted or substituted phenoxymethyl radical, an unsubstituted or substituted phenylthiomethyl or pyridylthiomethyl radical or a sulphoxide or sulphone thereof and $R^5$ is a carboxyl or a cyano group or an alkoxycarbonyl radical or an unsubstituted or substituted carboxamide group with, in each case, up to 21 carbon atoms and optionally further heteroatoms, such as oxygen, sulphur or nitrogen.

Typical examples of substituents on ester and amide functions include straight-chained and branched alkyl radicals containing up to 4 carbon atoms, especially methyl and ethyl radicals, unsubstituted and substituted benzyl radicals, unsubstituted or substituted aminoalkyl radicals, especially aminoethyl radicals, N-benzyl-N-alkylaminoalkyl radicals unsubstituted and substituted on the aromatic nucleus, N,N-dialkylaminoalkyl and N,N-dibenzylaminoalkyl radicals, as well as unsubstituted or substituted piperazinylalkyl and piperidinoalkyl radicals, N-substituted piperidyl radicals, lower alkylthioalkyl and alkoxyalkyl radicals.

Especially preferred are 1,6-naphthyridine derivatives of formula (I), in which $R^1$ is an unsubstituted phenyl radical or a phenyl radical substituted in the 2-position by halogen or trifluoromethyl or is an unsubstituted 1-naphthyl radical, $R^2$ is an isopropyl or 1-dimethylamino-2-propyl radical, $R^3$ is a hydrogen atom, $R^4$ is a methyl radical, an amino, cyano, formyl, hydroxyethoxymethyl, hydroxymethyl, halogenomethyl, dihalogenomethyl or methoxymethyl radical or an aminoethoxymethyl radical, phenylthiomethyl, 4-pyridylthiomethyl, phenylsulphinylmethyl or phenylsulphonylmethyl radical or a dimethylaminomethyl, dimethylaminoethoxymethyl, dimethylhydroxyethylammoniomethyl, N-methylpiperazinylmethyl, N-benzyl-N-methylaminoethoxymethyl, benzyloxymethyl, benzyloxyethoxymethyl or pyridinomethyl radical, $R^5$ is a cyano group or a methoxycarbonyl, ethoxycarbonyl or N-diphenylmethylpiperazinylethoxycarbonyl radical or a carboxamide radical of the formula

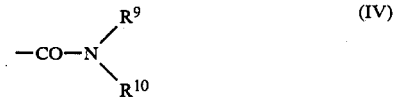

(IV)

wherein $R^9$ and $R^{10}$, which can be the same or different, are hydrogen atoms or ethyl or N-benzyl-N-methylaminoethyl radicals.

Furthermore, the present invention provides processes for the preparation of 1,6-naphthyridine derivatives of formula (I), wherein either (a) a 1,6-naphthyridinone derivative of formula

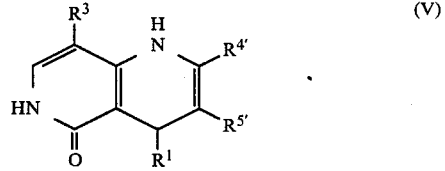

(V)

in which $R^1$ and $R^3$ have the above-given meanings, $R^{4'}$ is an alkyl radical containing up to 3 carbon atoms or an amino group and $R^{5'}$ is an alkoxycarbonyl radical containing up to 21 carbon atoms, which can also contain oxygen, sulphur or nitrogen atoms and is optionally substituted by carbocyclic or heterocyclic ring systems, is alkylated in known manner on the lactam oxygen; or (b) a 1,6-naphthyridine derivative of the formula

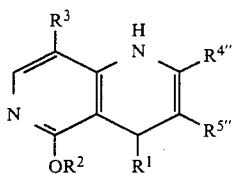

in which $R^1$, $R^2$ and $R^3$ have the above-given meanings, $R^{4''}$ is a methyl radical and $R^{5''}$ is a benzyloxy-carbonyl radical, is split hydrogenolytically in known manner to give the corresponding carboxylic acid and this, in turn, is reacted, via the intermediate stage of an acid halide, with an appropriately substituted alcohol or amine to give the corresponding ester or amide derivative of a 1,6-naphthyridine of formula (I); or (c) a 1,6-naphthyridine derivative of the formula

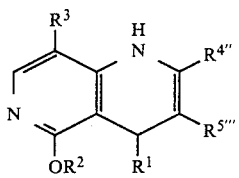

in which $R^1$, $R^2$, $R^3$ and $R^{4''}$ have the above-given meanings and $R^{5'''}$ is an alkoxycarbonyl radical or a substituted carboxamide radical with, in each case, up to 21 carbon atoms, which can also contain oxygen, sulphur or nitrogen atoms and is optionally substituted by carbocyclic or heterocyclic ring systems, is monobrominated on $R^{4''}$ and reacted with an appropriately substituted alcohol, thiol or primary, secondary or also tertiary amine and the product obtained is optionally converted by controlled oxidation into the corresponding sulphinyl or sulphonyl compound; or (d) a 1,6-naphthyridine derivative of formula (Ib) is dibromated on $R^{4''}$ and the dibromocompound formed is converted into another functional group, for example a formyl or cyano group; or (e) a 1,6-naphthyridinone derivative of formula V, in which $R^{5'}$ is a cyano and $R^{4'}$ a methyl group, which is prepared by reacting a compound of formula

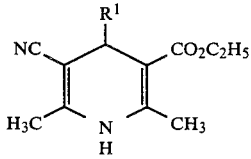

in which $R^1$ is as above, with s-triazine, is alkylated to a compound of formula I in which $R^5$ is a cyano and $R^4$ a methyl group. Compounds Va are prepared in analogous manner to known methods for preparing dihydropyridines.

1,6-Naphthyridine derivatives of formula (I), in which $R^5$ is an unsubstituted aminoalkylcarbonyl or aminoalkylcarbamoyl radical, can also be obtained by hydrogenolyticaly splitting in known manner a compound of formula (I), in which $R^5$ is an N,N-dibenzylaminoalkoxycarbonyl radical.

1,6-Naphthyridine derivatives of formula (I), in which $R^4$ is an unsubstituted aminoalkoxymethyl radical, can also be prepared by hydrogenolytically splitting in known manner compounds of general formula (I), in which $R^4$ is an N-benzylaminoalkoxymethyl or azidoalkoxymethyl radical.

The 1,6-naphthyridinones of formula (V) used for process (a) are described in German Pat. No. 33 27 650 or can be prepared in an analogous manner.

The preparation of 1,6-naphthyridine derivatives of formula (I) according to process (a) takes place, according to the present invention by means of the usual processes described in the literature for the O-alkylation of lactams (Adv. Heterocyclic Chem., 12, 185–212, 1970). Appropriate alkylation agents include alkyl halides, aminoalkyl halides, alkyl sulphonates, dialkyl sulphates and trialkoxyloxonium salts.

For the reaction with alkyl halides or aminoalkylhalides, the compounds of formula (V) are used in the form of their metal salts, preferably of their alkali metal, alkaline earth metal or silver salts, which are either separately prepared or are produced in situ with the help of appropriate bases, for example metal hydrides, carbonates or alkoxides, in an aprotic solvent.

As appropriate solvents, depending upon the particular alkylation agent used, there can be employed almost all inert organic solvents, such as open-chained, cyclic or also aromatic hydrocarbons, for example n-pentane, n-hexane, cyclohexane, benzene or toluene, halogenated hydrocarbons, for example dichloromethane or 1,2-dichloroethane, ethers, for example diethyl ether or 1,2-dimethoxyethane, as well as dipolar aprotic solvents, for example dimethylformamide, dimethylacetamide, hexamethylphosphoric acid triamide and dimethyl sulphoxide. Depending upon the solvent used, the temperature range can vary from −20° C. to the boiling point of the solvent used.

On the basis of the ambident character of the lactam anion, in the case of the alkylation according to process (a), there are frequently obtained mixtures of O- and N-alkylation products, depending upon the reaction conditions and the alkylation agents used (J. Org. Chem., 32, 4040 et seq., 1967). The separation of the product mixture obtained can take place by chromatographic methods and/or by crystallization.

The 1,6-naphthyridine derivatives of formula (I), in which $R^2$ is a methyl or ethyl radical, are preferably obtained by reaction of the 1,6-naphthyridinones of formula (V) with trimethyl or triethyloxonium salts, especially with trimethyloxonium or triethyloxonium tetrafluoroborate, in an aprotic solvent. The preparation of the O-propyl, O-isopropyl, O-sec-butyl, O-1-dimethylamino-2-propylor O-benzyl compounds, on the other hand, advantageously takes place by alkylation of the alkali metal, alkaline earth metal or silver salts with appropriate alkyl, aminoalkyl or benzyl halides.

The preparation of compounds of formula (I) according to process (b) from compounds of general formula (Ia), in which $R^{5''}$ is a benzyloxycarbonyl radical, preferably takes place, according to the present invention, by means of the processes described in the literature (for example, Houben-Weyl, Methoden der organischen Chemie, 4th edn., Vol. IV/1C, Reduction Part 1, 381–382, 1980).

For the hydrogenolysis of the benzyl esters, palladium on active charcoal is preferably used as catalyst. As solvent, there is preferably used a lower alcohol, especially methanol or ethanol. The temperature used can vary from 0° C. to the boiling point of the solvent used, it being preferred to work at atmospheric pressure and at a temperature of from 15° to 30° C. For the conversion of the carboxylic acid formed into a carboxylic acid halide, especially into a carboxylic acid chloride, there is a choice of various processes known from the literature. For the preparation of the carboxylic acid chlorides, it is especially preferred to use dimethyl-chloro-methylideneammonium chloride, which is formed from oxalyl chloride and dimethylformamide (Helv. Chim. Acta, 61, 1675–1681, 1978), or phosphorus pentachloride (Chem. Pharm. Bull., 28, 2809–2812, 1980).

In the case of the reaction of carboxylic acids with dimethylchloromethylideneammonium chloride, working is carried out under an atmosphere of nitrogen in an inert organic solvent, for example acetonitrile or dioxan, and at a temperature of from −30° to +30° C. but preferably at 0° C. The subsequent reaction of the carboxylic acid chlorides with appropriately substituted alcohols or amines takes place in a one-pot process at a temperature of from 0° to 50° C. and preferably at 20° C.

The reaction of the carboxylic acids with phosphorus pentachloride is carried out in solvents described in the literature for analogous reactions of carboxylic acids, preferably in chlorinated hydrocarbon, such as chloroform, dichloromethane, 1,2-dichloroethane or carbon tetrachloride, at a temperature of from −20° to +30° C. The further reaction to give esters and amides takes place in the manner described hereinbefore.

For the preparation of compounds of general formula (I) according to process (c) or (d), in which $R^4$ is a substituted alkyl radical, compounds of formula (I), in which $R^4$ is a methyl radical, are brominated with pyridinium bromide perbromide in the presence of a base, on the methyl radical (Synthesis, 1984, 617). The ratio of mono- to dibromination product is thereby controlled by the amount of pyridinium bromide perbromide used and by the reaction conditions. As base, there is used pyridine or an appropriate tertiary amine. Since the bases, depending upon the reaction conditions, partly react themselves with the monobromo compounds to give quaternary salts and can thus lead to side reactions, in the case of reactions in which the monobromo compound is to be subsequently reacted with an appropriately substituted primary, secondary or tertiary amine, this amine can already be used as the adjuvant base for the bromination. Appropriate solvents for the bromination are, in particular, chlorinated hydrocarbons, such as chloroform, dichloromethane, carbon tetrachloride or 1,2-dichloroethane.

For the preparation of the monobrominated compounds according to process (c), working is carried out at a temperature of from −40° to 0° C. and preferably at −20° C. The monobrominated compounds can be reacted in a one-pot process with solutions or suspensions of at least three equivalents of an appropriately substituted alcoholate, thiolate or primary, secondary or tertiary amine in an inert organic solvent. The alcoholates or thiolates are thereby preferably produced in situ from the corresponding alcohol or thiol with an appropriate base, for example sodium hydride, in a solvent, for example an open-chained or cyclic ether, preferably tetrahydrofuran, and this solution or suspension of the alcoholate or thiolate is reacted with the bromomethyl compound at a temperature of from −40° to +30° C.

The reaction products of the bromomethyl compounds with thiolates can be oxidized with one or two equivalents of a per acid, for example m-chloroperbenzoic acid, in an appropriate solvent, for example a chlorinated hydrocarbon, preferably dichloromethane, to give the corresponding sulphoxides or sulphones.

For the preparation of the dibromomethyl ompounds according to process (d), working is carried out with at least two equivalents of pyridinium bromide perbromide and at a temperature of from −20° to +20° C. The dibromomethyl compounds are isolated by chromatography and/or crystallization and optionally converted by known processes into other functional groups. Thus, compounds of formula (I), in which $R^4$ is a formyl group, are prepared by hydrolysis of the corresponding dibromomethyl compounds with silver nitrate, preferably in a mixture of water and a lower alcohol, for example methanol or ethanol, at a temperature of from 20° to 100° C.

Compound of formula (I), in which $R^4$ is a cyano group, are prepared from compounds of formula (I), in which $R^4$ is a formyl group, according to known processes, preferably with hydroxylamine or salts thereof in the presence of agents splitting off water, such as acetic anhydride (J. Sato, Fujisawa Pharmaceutical Co. Ltd., Belgian Pat. No. 879,263). Working is thereby carried out at a temperature of from 20° to 150° C. and preferably at 100° C. in glacial acetic acid.

Acidic or basic compounds of formula (I), in which $R^5$ is a carboxyl group or $R^4$ or $R^5$ has a basic center, are converted, for the purpose of purification or for galenical reasons, in crystalline, pharmacologically acceptable salts.

When $R^5$ is a carboxyl group, with the use of bases, for example of hydroxides or carbonates, there can be prepared the corresponding salts of alkali metals and alkaline earth metals. When the radicals $R^4$ and/or $R^5$ have a basic character, salts are obtained in the usual way by neutralization of the bases with appropriate inorganic or organic acids. As acids, there can be used, for example, hydrochloric acid, sulphuric acid, phosphoric acid, hydrobromic acid, acetic acid, tartaric acid, lactic acid, citric acid, malic acid, salicylic acid, ascorbic acid, malonic acid or succinic acid.

Since the compounds of formula (I) according to the present invention contain a chiral center on C-4, they can be present either as racemic mixtures or in the form of enantiomers.

The compounds of formula (I) according to the present invention are highly effective calcium antagonists.

Because of their blood vessel spasmolytic actions, they are particularly indicated in cases of cerebral, cardiac and peripheral blood vessel diseases. Therefore, the 1,6-naphthyridine derivatives according to the present invention are valuable agents for combating heart-circulation mortality.

The compounds of formula (I) according to the present invention can be administered orally or parenterally in liquid or solid form. As injection solution, water is preferably used which contains the additives usual in the case of injection solutions, such as stabilizing agents, solubilizing agents or buffers.

Additives of this kind include, for example, tartrate and citrate buffers, ethanol, complex formers (such as ethylenediamine-tetraacetic acid and the nontoxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol). Compositions suitable for oral administration can, if desired, contain additional flavoring and/or sweetening agents.

The individual doses administered enterally are in the range of from 5 to 250 mg and preferably of from 20 to 100 mg. About 1 to 20 mg are given parenterally.

The following examples are given for the purpose of illustrating the present invention:

EXAMPLE 1

Ethyl (±)-1,4-dihydro-5-isopropoxy-2-methyl-4-(2-thienyl)-1,6-naphthyridine-3-carboxylate 2.1 g (70 mMole) sodium hydride (80% in oil) are suspended in 100 ml dry dimethylformamide and, while stirring at ambient temperature, 20 g (63 mMole) ethy (±)-1,4,5,6-tetrahydro-2-methyl-5-oxo-4-(2-thienyl)-1,6-naphthyridine-3-carboxylate are added thereto portionwise. After cessation of the gas evolution, the reaction mixture is further stirred for 30 minutes at ambient temperature. 16 g (94 mMole) isopropyl iodide in 30 ml diemthylformamide are then added thereto. The reaction mixture is stirred for two days at ambient temperature, the solvent is removed in a vacuum and the residue is taken up with water and ethyl acetate. After shaking up, the ethyl acetate phase is separated off and dried over anhydrous magnesium sulphate. After distilling off the solvent, the residue obtained is separated chromatographically on silica gel with toluene/ethyl acetate (3:1 v/v). The fraction with the Rf of 0.3 is isolated and recrystallized from n-hexane. There is obtained ethyl (±)-1,4-dihydro-5-isopropoxy-2-methyl-4-(2-thienyl)-1,6-naphthyridine-3-carboxylate in the form of colorless crystals; mp 110°–111° C.

The ethyl (±)-1,4,5,6-tetrahydro-2-methyl-5-oxo-4-(2-thienyl)-1,6-naphthyridine-3-carboxylate used as starting material is prepared as follows:

A solution of 67 g (0.2 mole) diethyl 1,4-dihydro-2,6-dimethyl-4-(2-thienyl-pyridine-3,5-dicarboxylate in 300 ml dimethylformamide is added dropwise to a suspension of 6 g (0.2 mole) sodium hydride (80% in oil) in 100 ml dry dimethylformamide under an atmosphere of nitrogen. Upon subsidence of the gas evolution, the reaction mixture is further stirred for ten minutes at ambient temperature and subsequently 16.2 g (0.2 mole) s-triazine in 300 ml dimethylformamide are added dropwise thereto. The reaction mixture is heated for 16 hours to 110° C. and, after cooling, evaporated in a vacuum. The residue is chromatographed on silica gel with dichloromethane/methanol (9:1 v/v). The fraction with the Rf of 0.4 is isolated and recrystallized from ethanol. There is obtained ethyl (±)-1,4,5,6-tetrahydro-2-methyl-5-oxo-4-(2-thienyl)-1,6-naphthyridine-3-carboxylate in the form of pale brown crystals; mp 284°–285° C.

The following compounds are obtained in an analogous manner:
ethyl (±)-1,4-dihydro-5-isopropoxy-2-methyl-4-(1-naphthyl)-1,6-naphthyridine-3-carboxylate (1.a) mp 204°–206° C., recrystallized from diisopropyl ether/ethanol
ethyl (±)-2-amino-1,4-dihydro-5-isopropoxy-4-(2-trifluoromethylphenyl)-1,6-naphthyridine-3-carboxylate (1.b)
mp 173°–175° C. from n-hexane/diisopropyl ether
2-[1-(4-diphenylmethylpiperazinyl)]-ethyl (±)-1,4-dihydro-5-isopropoxy-2-methyl-4-(2-trifluoromethylphenyl)-1,6-naphthyridine-3-carboxylate.5 oxalate (1.c)
mp>110° C. (decomp.) from ethyl acetate/isopropanol.

EXAMPLE 2

Methyl (±)-1,4-dihydro-5-isopropoxy-2-[(4-methyl-piperazin-1-yl)-methyl]-4-phenyl-1,6-naphthyridine-3-carboxylate.

1.0 g (3.0 mMole) methyl (±)-1,4-dihydro-5-isopropoxy-2-methyl-4-phenyl-1,6-naphthyridine-3-carboxylate (for the preparation cf. Federal Republic of Germany Patent Specification No. 34 31 303) in ethanol-free chloroform is cooled to −10° C., mixed with 0.26 ml (3.2 mMole) pyridine and subsequently portionwise with 1.1 g (3.1 mMole) pyridinium bromide perbromide (90%). After 30 minutes at −10° C., 0.62 g (6.2 mMole) N-methylpiperazine is added dropwise thereto and the reaction mixture is stirred for 15 minutes at −10° C. and then warmed to 20° C. within the course of one hour. The reaction mixture is diluted with chloroform, washed with water and the organic phase is dried over anhydrous sodium sulphate. The residue obtained after distilling off the solvent is chromatographed on silica gel with dichloromethane/methanol (9:1 v/v). The fraction with the Rf of 0.3 is recrystallized from n-hexane. There is obtained methyl (±)-1,4-dihydro-5-isopropoxy-2-[(4-methyl-piperazin-1-yl)-methyl]-4-phenyl-1,6-naphthyridine-3-carboxylate in the form of colorless crystals; mp 149°–151° C.

The following compounds are obtained in an analogous manner:
ethyl (±)-2-dimethylaminomethyl-1,4-dihydro-5-isopropoxy-4-(2-trifluoromethylphenyl)-1,6-naphtyridine-3-carboxylate dihydrochloride (2.a)
mp 169°–172° C. (decomp.), recrystallized from ethyl acetate/isopropanol
(±)-[3-ethoxycarbonyl-1,4-dihydro-5-isopropoxy-4-(2-trifluoromethylphenyl)-1,6-naphthyridin-2-yl]-methyl-1-pyridinium bromide (2.b)
mp 206°–207° C., recrystallized from isopropanol
(±)-[3-ethoxycarbonyl-1,4-dihydro-5-isopropoxy-4-(1-naphthyl)-1,6-naphthyridin-2-yl]-methyl-(2-hydroxyethyl)-dimethylammonium bromide (2.c)
mp 212°–215° C., recrystallized from ethyl acetate/isopropanol.

EXAMPLE 3

Ethyl (±)-2-(2-aminoethoxymethyl)-4-(2-chlorophenyl)-1,4-dihydro-5-isopropoxy-1,6-naphthyridine-3-carboxylate dihydrochloride A solution of 5.0 g (12.9 mMole) ethyl (±)-4-(2-chlorophenyl)1,4-dihydro-5-isopropoxy-2-methyl-1,6-napthyridine-3-carboxylate (for the preparation cf. Federal Republic of Germany Patent Specification No. 335 02 790) in 75 ml dichloromethane is cooled to −20° C., mixed with 1.1 ml (13.6 mMole) pyridine and subsequently portionwise with 5.0 g (14.1 mMole) pyridinium bromide perbromide (90%). The reaction mixture is then stirred for one hour at −20° C.

Parallel thereto, a solution of 2.6 g (42.6 mMole) 2-aminoethanol in 100 ml tetrahydrofuran is mixed portionwise at 20° C. with 1.3 g (43.3 mMole) sodium hydride (80% in oil). After completion of the evolution of hydrogen, this solution is added dropwise to the solution obtained of ethyl (±)-2-bromomethyl-4-(2-chlorophenyl)-1,4-dihydro-5-isopropoxy-1,6-naphthyridine-3-carboxylate, cooled to −20° C. The reaction mixture is warmed to ambient temperature and stirred for one hour at 20° C. After the addition of 300 ml water, it is shaken up and the organic phase is separated off and dried over anhydrous sodium sulphate. The residue obtained after distilling off the solvent is chromatographed on silica gel with dichloromethane/methanolic ammonia solution (95:5 v/v). The fraction with the Rf of 0.3 is isolated, dissolved in diethyl ether/ethyl acetate and the dihydrochloride precipitated out with hydrogen chloride in diethyl ether. After recrystallization from isopropanol, there is obtained ethyl (±)-2-(2-aminoethoxymethyl)-4-(2-chlorophenyl)-1,4-dihydro-5-isopropoxy-1,6-naphthyridine-3-carboxylate dihydrochloride in the form of colorless crystals; mp 187°–188° C.

The following compound is obtained in an analogous manner:

ethyl (±)-2-(2-aminoethoxymethyl)-1,4-dihydro-5-isopropoxy-4-(2-trifluoromethylphenyl)-1,6-naphthyridine-3-carboxylate hydrochloride (3.a)
mp 200°–203° C. (decomp.), recrystallized from acetonitrile ethyl (±)-1,4-dihydro-5-isopropoxy-2-methoxymethyl-4-(2-trifluoromethylphenyl)-1,6-naphthyridine-3-carboxylate (3.b)
mp 161°–162° C., recrystallized from n-hexane ethyl (±)-1,4-dihydro-2-hydroxymethyl-5-isopropoxy-4-(2-trifluoromethylphenyl)1,6-naphthyridine-3-carboxylate (3.c)
mp 150°–152° C. recrystallized from n-hexane/diisopropyl ether ethyl (±)-1,4-dihydro-5-isopropoxy-2-phenylthiomethyl-4-(2-trifluoromethylphenyl)-2,6-naphthyridine-3-carboxylate (3.d)
mp 75°–76° C., recrystallized from n-hexane ethyl (±)-1,4-dihydro-5-isopropoxy-2-(4-pyridylthiomethyl)-4-(2-trifluoromethylphenyl)-1,6-naphthyridine-3-carboxylate (3.e)
mp 214°–216° C., recrystallized from ethyl acetate ethyl (±)-4-(2-chlorophenyl)-1,4-dihydro-2-hydroxymethyl-5-isopropoxy-1,6-naphthyridine-3-carboxylate (3.f)
mp 183°–186° C., recrystallized from n-hexane/diisopropyl ether ethyl (±)-2-(2-N-benzyl-N-methylaminoethoxymethyl)-1,4-dihydro-5-isopropoxy-4-(2-trifluoromethylphenyl)-1,6-naphthyridine-3-carboxylate . dioxalate (3.g)
mp 126°–128° C., recrystallized from ethyl acetate ethyl (±)-2-(2-dimethylaminoethoxymethyl)-1,4-dihydro-5-isopropoxy-4-(1-naphthyl)-1,6-naphthyridine-3-carboxylate (3.h)
mp 134°–137° C., recrystallized from diisopropyl ether/ethyl acetate ethyl (±)-2-(benzyloxyethoxymethyl)-1,4-dihydro-5-isopropoxy-4-(2-trifluoromethylphenyl)-1,6-naphthyridine-3-carboxylate (3.i)
mp 99°–101° C., recrystallized from n-hexane ethyl (±)-2-(2-benzyloxymethyl)-1,4-dihydro-5-isopropoxy-4-(2-trifluoromethylphenyl)-1,6-naphthyridine-3-carboxylate (3.j)
mp 94°–95° C., recrystallized from n-hexane.

EXAMPLE 4

Ethyl (±)-2-dibromomethyl-1,4-dihydro-5-isopropoxy-4-phenyl-1,6-naphthyridine-3-carboxylate 10.g (28.4 mMole) ethyl (±)-1,4-dihydro-5-isopropoxy-2-methyl-4-phenyl-1,6-naphthyridine-3-carboxylate (for the preparation cf. Federal Republic of Germany Patent Specification No. 35 02 790) in 160 ml ethanol-free chloroform are cooled to 0° and mixed with 4.6 ml (56.8 mMole) pyridine and subsequently portionwise with 20.2 g (56.8 mMole) pyridinium bromide perbromide (90%). The reaction mixture is stirred for 30 minutes at 0° C., then heated under reflux for 15 minutes. After cooling, the reaction mixture is diluted with chloroform, washed with 2 N hydrochloric acid and then with water and the organic phase is dried over anhydrous magnesium sulphate. The residue obtained after evaporation is chromatographed on silica gel with dichloromethane/methanol (9:1 v/v). Ethyl (±)-2-dibromomethyl-1,4-dihydro-5-isopropoxy-4-phenyl-1,6-naphthyridine-3-carboxylate is isolated, as the fraction with the Rf of 0.7, in the form of a pale yellow oil.

The following compound is obtained in an analogous manner:

methyl (±)-4-(2-bromophenyl)-2-dibromomethyl-1,4-dihydro-5-isopropoxy-1,6-naphthyridine-3-carboxylate (4.a)
mp 144°–146° C., recrystallized from n-pentane.

EXAMPLE 5

(±)-1,4-Dihydro-5-isopropoxy-2-methyl-4-(2-trifluoromethylphenyl)-1,6-naphthyridine-3-carboxylic acid 2-(N-benzyl-N-methylamino)-ethylamide dihydrochloride 17 ml dry dimethylformamide in 40 ml dry dioxan are cooled to 0° C. and 1.0 g (7.9 mMole) oxalyl chloride added dropwise thereto under an atmosphere of nitrogen. After 20 minutes, 2.7 g (6.9 mMole) (±)-1,4-dihydro-5-isopropoxy-2-methyl-4-(2-trifluoromethylphenyl)-1,6-naphthyridine-3-carboxylic acid (European Patent Application 173 933) are added portionwise thereto at 0° C. and the reaction mixture is warmed to 20° C. After 30 minutes at 20° C., this solution is added dropwise to a solution, cooled to 0° C., of 2.6 g (15.8 mMole) N-benzyl-N-methylethylene-diamine in 20 ml n-hexane. After warming to 20° C., the reaction mixture is stirred for 30 minutes then, with renewed ice cooling, 2 N aqueous sodium carbonate solution is added dropwise thereto and the reaction mixture is extracted twice with dichloromethane. The dichloromethane solutions are washed with water and dried over anhydrous sodium sulphate. The solvent is removed in a vacuum and the residue is chromatographed on silica gel with dichloromethane/methanol (9:1 v/v). The fraction with the Rf of 0.5 is isolated, dissolved in diethyl ether and the dihydrochloride precipitated out with hydrogen chloride in diethyl ether. This is recrystallized twice from acetonitrile. There is obtained (±)-1,4-dihydro-5-isopropoxy-2-methyl-4-(2-trifluoromethylphenyl)-1,6-naphthyridine-3-carboxylic acid 2-(N-benzyl-N-methylamino)-ethylamide dihydrochloride in the form of colorless crystals; mp 178°–180° C.

The following compounds are obtained in an analogous manner:

(±)-1,4-dihydro-5-isopropoxy-2-methyl-4-(2-trifluoromethylphenyl)-1,6-naphthyridine-3-carboxylic acid N-ethylamide (5.a)
mp 221°–224° C. from ethyl acetate (±)-1,4-dihydro-5-isopropoxy-2-methyl-4-(2-trifluoromethylphenyl)-1,6-naphthyridine-3-carboxylic acid amide (5.b)
mp 270°–271° C. from ethyl acetate.

EXAMPLE 6

Ethyl (±)-1,4-dihydro-5-isopropoxy-2-phenylsulphinyl-methyl-4-(2-trifluoromethylphenyl)-1,6-naphthyridine-3-carboxylate A solution of 1.0 g (1.9 mMole) ethyl (±)-1,4-dihydro-5-isopropoxy-2-phenylthiomethyl-4-(2-trifluoromethylphenyl)-1,6-naphthyridine-3-carboxylate (Example 3.d) in 30 ml dichloromethane is cooled to 0° C. and 0.4 g (2.1 mMole) 3-chloroperoxy-benzoic acid (90%) is added portionwise thereto. After 10 minutes at 0° C., an aqueous solution of sodium hydrogen carbonate is added dropwise thereto and the organic phase is separated off, washed with water and dried over anhydrous sodium sulphate. After distilling off the solvent, the residue obtained is recrystallized from ethyl acetate. There is obtained ethyl (±)-1,4-dihydro-5-isopropoxy-2-phenylsulphinylmethyl-4-(2-trifluoromethylphenyl)-1,6-naphthyridine-3-carboxylate in the form of colorless crystals; mp 206°–208° C.

EXAMPLE 7

Ethyl (±)-1,4-dihydro-5-isopropoxy-2-phenylsulphonyl-methyl-4-(2-trifluoromethylphenyl)-1,6-naphthyridine-3-carboxylate The crude product obtained by the reaction of ethyl (±)-1,4-dihydro-5-isopropoxy-2-phenylthiomethyl-4-(2-trifluoromethylphenyl)-1,6-naphthyridine-3-carboxylate (Example 3.d) with 2 equivalents of 3-chloroperoxybenzoic acid and a reaction period of 16 hours at 20° C., carried out analogously to Example 6, is separated chromatographically on silica gel with toluene/ethyl acetate (3:1 v/v). The fraction with the Rf of 0.3 is isolated and recrystallized from diisopropyl ether. There is obtained ethyl (±)-1,4-dihydro-5-isopropoxy-2-phenylsulphonylmethyl-4-(2-trifluoromethylphenyl)-1,6-naphthyridine-3-carboxylate in the form of colorless crystals; mp 177°–182° C.

EXAMPLE 8

Ethyl (±)-2-formyl-1,4-dihydro-5-isopropoxy-4-phenyl-1,6-naphthyridine-3-carboxylate A solution of 3.1 g (6.1 mMole) ethyl (±)-2-dibromomethyl-1,4-dihydro-5-isopropoxy-4-phenyl-1,6-naphthyridine-3-carboxylate (Example 4) in 70 ml ethanol is heated to 60° C. and, at this temperature, a solution of 2.1 g (12.4 mMole) silver nitrate in 5 ml water/3 ml ethanol is added dropwise thereto. The reaction mixture is heated under reflux for ten minutes, cooled and the precipitate filtered off, whereafter the filtrate is evaporated. After dilution with dichloromethane, it is washed with water and the organic phase is dried over anhydrous magnesium sulphate and subsequently evaporated in a vacuum. The residue is chromatographed on silica gel with toluene/ethyl acetate (9:1 v/v). The fraction with the Rf of 0.3 is isolated and recrystallized from n-hexane/cyclohexane. There is obtained ethyl (±)-2-formyl-1,4-dihydro-5-isopropoxy-4-phenyl-1,6-naphthyridine-3-carboxylate in the form of yellow crystals; mp 132°–135° C.

The following compound is obtained in an analogous manner:
ethyl (±)-2-formyl-1,4-dihydro-5-isopropoxy-4-(2-trifluoromethylphenyl)-1,6-naphthyridine-3-carboxylate (8.a)
mp 108°–109° C. from n-hexane.

EXAMPLE 9

Ethyl (±)-2-cyano-1,4-dihydro-5-isopropoxy-4-(2-trifluoromethylphenyl)-1,6-naphthyridine-3-carboxylate A solution of 1 g (2.30 mMole) ethyl (±)-2-formyl-1,4-dihydro-5-isopropoxy-4-(2-trifluoromethylphenyl)-1,6-naphthyridine-3-carboxylate (Example 8.a) in 15 ml acetic acid is stirred for 2.5 hours at 20° C. with 0.29 g (3.54 mMole) anhydrous sodium acetate and 0.22 g (3.17 mMole) hydroxylamine hydrochloride. 0.80 ml (8.46 mMole) acetic anhydride are added and stirring is continued for additional 1.5 hours at 20° C. and thereafter for ten hours at 100° C. The solution is evaporated in a vacuum and the residual oily liquid is dilated with 50 ml water, neutralized with saturated potassium hydrogen carbonate solution and extracted twice with 30 ml dichloromethane. The dichloromethane solution is dried over anhydrous sodium sulphate and filtered. After distilling off the solvent, the residue obtained is separated chromatographically on silica gel with toluene/ethyl acetate (9:1 v/v). The fraction with the Rf of 0.2 is isolated and recrystallized from n-hexane.

There is obtained ethyl (±)-2-cyano-1,4-dihydro-5-isopropoxy-4-(2-trifluoromethylphenyl)-1,6-naphthyridine-3-carboxylate in the form of pale yellow crystals; mp 138°–140° C.

EXAMPLE 10

(±)-1,4-Dihydro-5-isopropoxy-2-methyl-4-(2-trifluoromethylphenyl)-1,6-naphthyridine-3-carbonitrile 8.0 g (24.1 mMole) of (±)-1,4,5,6-tetrahydro-2-methyl-5-oxo-4-(2-trifluoromethylphenyl)-1,6-naphthyridine-3-carbonitrile is heated for ten hours at 100° C. with 5.0 g (50.0 mMole) calcium carbonate and 12.5 g (73.5 mMole) isopropyl iodide in 100 ml dimethylacetamide. After cooling the solvent is evaporated in a vacuum. The residue is extracted with 100 ml water and 100 ml dichloromethane. The organic phase is separated, dried over sodium sulphate and the solvent is distilled off. The residue obtained is separated chromatographically on silica gel with toluene ethyl acetate (1:1 v/v). The fraction with the Rf of 0.35 is isolated and recrystallized from diisopropyl ether/ethyl acetate.

There is obtained (±)-1,4-dihydro-5-isopropoxy-2-methyl-4-(2-trifluoromethylphenyl)-1,6-naphthyridine-3-carbonitrile in the form of colorless crystals, mp 207°–209° C.

(±)-1,4,5,6-Tetrahydro-2-methyl-5-oxo-4-(2-trifluoromethylphenyl)-1,6-naphthyridine-3-carbonitrile used as starting material is prepared as follows:

To a suspension of 4.5 g (0.15 Mole) sodium hydride (80% in oil) in 50 ml dry dimethylformamide is added under an atmosphere of nitrogen a solution of 43.7 g (0.12 Mole) ethyl (±)-5-cyano-1,4-dihydro-2, 6-dimethyl-4-(2-trifluoromethylphenyl)-pyridine-3-carboxylate in 150 ml dimethylformamide. Upon subsidence of the gas evolution, the reaction mixture is further stirred for ten minutes at ambient temperature and subsequently 10.1 g (0.12 Mole) s-triazine in 200 ml dimethylformamide are added dropwise. The reaction mixture is heated for 16 hours to 100° C. and, after cooling, evaporated in a vacuum. The residue is chromatographed on silica gel with dichloromethane/methanol (9:1 v/v). The fraction with the Rf of 0.4 is isolated and recrystallized from ethanol.

There is obtained (±)-1,4,5,6-tetrahydro-2-methyl-5-oxo-4-(2-trifluoromethylphenyl)-1,6-naphthyridine-3-carbonitrile in the form of beige crystals; mp >290° C. (decomp.).

Ethyl (±)-5-cyano-1,4-dihydro-2,6-dimethyl-4-(2-trifluoromethylphenyl)-pyridine-3-carboxylate used as starting material is prepared in analogous manner to known preparational methods for dihydropyridine from ethyl-2'-trifluoromethylbenzylidene acetoacetate and 3-aminocrotonitrile by boiling in isopropanol for five hours.

EXAMPLE 11

Ethyl (±)-1,4-dihydro-5-(1-dimethylamino-2-propoxy)-2-methyl-4-(2-trifluoromethylphenyl)-1,6-naphthyridine-3-carboxylate.dihydrochloride 20 g (53 mMole) ethyl (±)-1,4,5,6-tetrahydro-2-methyl-5-oxo-4-(2-trifluoromethylphenyl)-1,6-naphthyridine-3-carboxylate (German Patent Application No. P 33 27 650, Example 5) is stirred with 10.6 g (106 mMole) calcium carbonate, 20 g (160 mMol) 1-dimethylamino-2-propylchloride and a catalytic amount of potassium iodide in 200 ml dimethylacetamide for 16 hours at 100° C. After cooling and filtration the solvent is evaporated in a vacuum. The residue is extracted with 100 ml in sodium hydroxide solution and 100 ml dichloromethane. The organic phase is separated, washed with water, dried over sodium sulphate and the solvent is distilled off. The residue is chromatographed on silica gel with dichloromethane/methanol (9:1 v/v) and the fraction with the Rf of 0.2 is isolated. The fraction is dissolved in 100 ml ether and the dihydrochloride is precipitated with hydrogen chloride in ether, filtered off and recrystallized from ethyl acetate/ethanol.

There is obtained ethyl (±)-1,4-dihydro-5-(1-dimethylamino-2-propoxy)-2-methyl-4-(2-trifluoromethylphenyl)-1,6-naphthyridine-3-carboxylate dihydrochloride in the form of pale beige crystals; mp 153°-156° C.

EXAMPLE 12

Ethyl (±)-1,4-dihydro-2-(2-hydroxyethoxymethyl)-5-isopropoxy-4-(2-trifluoromethylphenyl)-1,6-naphthyridine-3-carboxylate 2.75 g (4.82 mMole) ethyl (±)-2-(2-benzyloxyethoxymethyl)-1,4-dihydro-5-isopropoxy-4-(2-trifluoromethylphenyl)-1,6-naphthyridine-3-carboxylate (Example 3.1) are hydrogenated at normal pressure and at 50° C. in the presence of 1.3 of 10% palladium on active charcoal in 250 ml ethanol. The catalyst is filtered off subsequently after the hydrogen take up is finished. The solvent is distilled off from the filtrate in a vacuum and the residue is recrystallized from n-hexane.

There is obtained ethyl (±)-1,4-dihydro-2-(2-hydroxyethoxymethyl)-5-isopropoxy-4-(2-trifluoromethylphenyl)-1,6-naphthyridine-3-carboxylate in the form of colorless crystals; mp 109°-112° C.

We claim:

1. A compound named Ethyl (±)-2-(2-aminoethoxymethyl)-4-(2-chlorophenyl)-1,4-dihydro-5-isopropoxy-1,6-naphthyridine-3-carboxylate or a pharmaceutically acceptable salt thereof.

2. A compound named Ethyl (±)-2-dibromomethyl-1,4-dihydro-5-isopropoxy-4-phenyl-1,6-naphthyridine-3-carboxylate or a pharmaceutically acceptable salt thereof.

3. A compound named (±)-1,4-Dihydro-5-isopropoxy-2-methyl-4-(2-trifluoro-methylphenyl)-1,6-naphthyridine-3-carboxylic acid 2-(N-benzyl-N-methylamino)-ethylamide or a pharmaceutically acceptable salt thereof.

4. A compound named Ethyl (±)-1,4-dihydro-5-isopropoxy-2-phenyl-sulphinyl-methyl-4-(2-trifluoromethylphenyl)-1,6-naphthyridine-3-carboxylate or a pharmaceutically acceptable salt thereof.

5. A compound named Ethyl (±)-1,4-dihydro-5-isopropoxy-2-phenylsulphonyl-methyl-4-(2-trifluoromethylphenyl)-1,6-naphthyridine-3-carboxylate and a pharmaceutically acceptable salt thereof.

6. A compound named Ethyl (±)-2-formyl-1,4-dihydro-5-isopropoxy-4-phenyl-1,6-napthyridine-3-carboxylate or a pharmaceutically acceptable salt thereof.

7. A compound named Ethyl (±)-2-cyano-1,4-dihydro-5-isopropoxy-4-(2-trifluoromethylphenyl)-1,6-naphthyridine-3-carboxylate or a pharmaceutically acceptable salt thereof.

8. A compound named (±)-1,4-Dihydro-5-isopropoxy-2-methyl-4-(2-trifluoromethylphenyl)-1,6-naphthyridine-3-carbonitrile or a pharmaceutically acceptable salt thereof.

9. A compound named Ethyl (±)-1,4-dihydro-5-(1-dimethylamino-2-propoxy)-2-methyl-4-(2-trifluoromethylphenyl)-1,6-naphthyridine-3-carboxylate or a pharmaceutically acceptable salt thereof.

10. A compound named Ethyl (±)-1,4-dihydro-2-(2-hydroxyethoxymethyl)-5-isopropoxy-4-(2-trifluoromethylphenyl)-1,6-naphthyridine-3-carboxylate or a pharmaceutically acceptable salt thereof.

* * * * *